United States Patent [19]

Lesher et al.

[11] 4,304,777

[45] Dec. 8, 1981

[54] 6-(PYRIDINYL)-3(2H)-PYRIDAZINONES AND THEIR USE AS CARDIOTONICS

[75] Inventors: George Y. Lesher, Schodack; William B. Dickinson, Albany, both of N.Y.

[73] Assignee: Sterling Drug Inc., New York, N.Y.

[21] Appl. No.: 144,576

[22] Filed: Apr. 28, 1980

Related U.S. Application Data

[63] Continuation-in-part of Ser. No. 71,065, Aug. 30, 1979, abandoned.

[51] Int. Cl.$^3$ .................. C07D 237/14; A01K 31/50
[52] U.S. Cl. .................................. 424/250; 544/239
[58] Field of Search ...................... 424/250; 544/239

[56] References Cited

U.S. PATENT DOCUMENTS

| | | | |
|---|---|---|---|
| 3,746,712 | 7/1973 | Ross | 424/250 |
| 3,812,256 | 5/1974 | Curran | 424/250 |
| 3,822,260 | 7/1974 | Curran et al. | 424/250 |
| 4,004,009 | 1/1977 | Andersen | 544/239 |
| 4,004,012 | 1/1977 | Lesher et al. | 424/263 |
| 4,072,746 | 2/1978 | Lesher et al. | 424/263 |
| 4,107,315 | 8/1978 | Lesher et al. | 424/263 |
| 4,137,233 | 1/1979 | Lesher et al. | 546/257 |
| 4,199,586 | 4/1980 | Lesher et al. | 424/263 |

FOREIGN PATENT DOCUMENTS 54-19987  2/1979  Japan.

OTHER PUBLICATIONS

Curran et al. II, J. Med. Chem. 17, 273 (1974).
Haginiwa et al., Chem. Abs. 88, 170096 (1978).
Steck et al., J. Amer. Chem. Soc., 75, 1117 (1953).

*Primary Examiner*—Mark L. Berch
*Attorney, Agent, or Firm*—Robert K. Bair; B. Woodrow Wyatt

[57] ABSTRACT

2-R-6-PY-3(2H)-pyridazinones (I) or salts thereof, which are useful as cardiotonics, where R is hydrogen, lower-alkyl or lower-hydroxyalkyl, and PY is 4- or 3-pyridinyl or 4- or 3-pyridinyl having one or two lower-alkyl substituents, are prepared by reacting 2-R-4,5-dihydro-6-PY-3(2H)-pyridazinone with a dehydrogenating agent. Also shown are: cardiotonic compositions and a method for increasing cardiac contractility using I or salts; and, the preparation of the corresponding intermediate 4,5-dihydro compounds.

16 Claims, No Drawings

6-(PYRIDINYL)-3(2H)-PYRIDAZINONES AND THEIR USE AS CARDIOTONICS

CROSS-REFERENCE TO RELATED APPLICATION

This application is a continuation-in-part of copending application Ser. No. 71,065, filed Aug. 30, 1979 and now abandoned.

4,5-Dihydro-6-(4-pyridinyl)-3-pyridazinol, tautomeric with 4,5-dihydro-6-(4-pyridinyl)-3(2H)-pyridazinone, is disclosed and claimed in copending application Ser. No. 71,064, filed Aug. 30, 1979. Also disclosed and claimed is the process which comprises reacting γ-oxo-γ-(4-pyridinyl)butyronitrile with a hydrazine salt of a strong inorganic or organic sulfonic acid to produce 4,5-dihydro-6-(4-pyridinyl)-3-pyridazinol. Also shown and claimed is the use of 4,5-dihydro-6-(4-pyridinyl)-3-pyridazinol in lowering blood pressure. 4,5-Dihydro-6-(4-pyridinyl)-3-pyridazinol or tautomeric 4,5-dihydro-6-(4-pyridinyl)-3(2H)-pyridazinone also is disclosed as an intermediate in copending U.S. Patent appliction Ser. No. 144,563, filed Apr. 28, 1980.

Copending U.S. Patent application Ser. No. 144,564, filed Apr. 28, 1980, discloses and claims 2-R-4,5-dihydro-6-PY-3(2H)-pyridazinones and their use as cardiotonics, where R is lower-alkyl or lower-hydroxyalkyl and PY is 4- or 3-pyridinyl or 4- or 3-pyridinyl having one or two lower-alkyl substituents. Said 2-R-4,5-dihydro-6-PY-3(2H)-pyridazinones also are disclosed as intermediates in copending U.S. Patent application Ser. No. 144,563, filed Apr. 28, 1980.

6-(4-Pyridinyl)-3-pyridazinol, tautomeric with 6-(4-pyridinyl)-3(2H)-pyridazinone and its preparation from 4,5-dihydro-6-(4-pyridinyl)-3-pyridazinol are disclosed and claimed in copending application Ser. No. 71,065, abandoned, filed Aug. 30, 1979. Also shown and claimed is the use of 6-(4-pyridinyl)-3-pyridazinol as a cardiotonic. 6-(4-Pyridinyl-3-pyridazinol or tautomeric 6-(4-pyridinyl)-3(2H)-pyridazinone also is disclosed as an intermediate in copending U.S. Patent application Ser. No. 144,563, filed Apr. 28, 1980.

BACKGROUND OF THE INVENTION (a) Field of the invention

This invention relates to 6-(pyridinyl)-3(2H)-pyridazinones, useful as cardiotonic agents, to their preparation, and to their use as cardiotonic agents.

(b) Description of the Prior Art

Haginiwa et al. [Yakugaku Zasshi 98 (1), 67–71 (1978); Chem. Abstrs. 88, 170,096v (1978)] reacted 3(2H)-pyridazinone with pyridine 1-oxide and platinized Pd-C catalyst to produce 6-(2-pyridinyl)-3(2H)-pyridazinone.

Yoshitomi Pharmaceutical Ind., Ltd. Japanese Patent Application Disclosure No. 19,987/79, published Feb. 15, 1979 and based on Application No. 85,192/77, filed July 15, 1977, discloses, inter alia, the preparation of 4,5-dihydro-6-(4-pyridinyl)-3(2H)-pyridazinone by refluxing for two hours an ethanolic solution of 3-(isonicotinoyl)propanoic acid [same as γ-oxo-γ-(4-pyridinyl)butyric acid] and hydrazine hydrate. 4,5-Dihydro-6-(4-pyridinyl)-3(2H)-pyridazinone and closely related 4,5-dihydro-6-(4- or 3- or 2-pyridinyl)-5-R-3(2H)-pyridazinones, where R is H or lower alkyl, are said (page 2 of English translation) to be "useful not only as medicines such as hypotensive and antithrombus agents because they have pharmacological actions such as hypotensive, blood platelet coagulation-inhibitory and membrane-stabilizing actions, but also as intermediates for the synthesis of such medicines".

Steck et al. [J. Am. Chem. Soc. 75, 1117–9 (1953)] show the dehydrogenation of 4,5-dihydro-6-(halophenyl)-3-pyridazones (pyridazones formerly used to designate pyridazinones) by the action of bromine in acetic acid to produce 6-(halophenyl)-3-pyridazones.

SUMMARY OF THE INVENTION

In a composition of matter aspect, the invention relates to 2-R-6-PY-3(2H)-pyridazinones (I) or pharmaceutically-acceptable acid-addition salts thereof, useful as cardiotonic agents, to their preparation and to their use as intermediates and/or as cardiotonics, where R and PY are defined hereinbelow.

In a process aspect the invention comprises dehydrogenating 2-R-4,5-dihydro-6-PY-3(2H)-pyridazinone to produce 2-R-6-PY-3(2H)-pyridazinone.

A composition aspect of the invention relates to a cardiotonic composition for increasing cardiac contractility, said composition comprising a pharmaceutically-acceptable inert carrier and, as the active component thereof, an effective amount of the cardiotonic 2-R-6-PY-3(2H)-pyridazinone or pharmaceutically-acceptable acid-addition salt thereof.

In a method aspect, the invention relates to a method for increasing cardiac contractility in a patient requiring such treatment which comprises administering orally or parenterally in solid or liquid dosage form to such patient an effective amount of the cardiotonic 2-R-6-PY-3(2H)-pyridazinone or pharmaceutically-acceptable acid-addition salt thereof.

DETAILED DESCRIPTION INCLUSIVE OF PREFERRED EMBODIMENTS

In a composition of matter aspect the invention resides in the 2-R-6-PY-3(2H)-pyridazinones having formula I

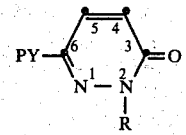

or pharmaceutically-acceptable acid-addition salt thereof, where PY is 4- or 3-pyridinyl or 4- or 3-pyridinyl having one or two lower-alkyl substituents, and R is hydrogen, lower-alkyl or lower-hydroxyalkyl. The compounds of formula I are useful as cardiotonic agents, as determined by standard cardiotonic evaluation procedures. Also, the compounds of formula I are disclosed as intermediates, in copending application Ser. No. 144,563, filed Apr. 28, 1980. Preferred embodiments are those of formula I where R is hydrogen, methyl, ethyl, or 2-hydroxyethyl and PY is 4-pyridinyl or 3-pyridinyl.

The compounds of formula I where R is hydrogen may exist in tautomeric forms, that is, as 6-PY-3(2H)-pyridazinones of formula I and/or as 6-PY-3-pyridazinols of formula IA, illustrated as follows

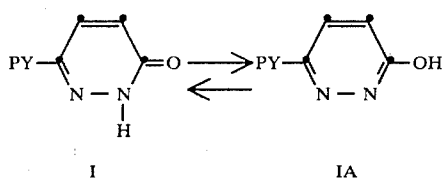

Structural preferences are known 3(2H)-pyridazinones or 3-pyridazinols would indicate the above formula I to be the preferred tautomeric structure; thus, we have preferred to use the names based on structure I, although it is understood that either or both structures are comprehended herein.

In a process aspect the invention resides in the process of producing 2-R-6-PY-3(2H)-pyridazinone which comprises reacting 2-R-4,5-dihydro-6-PY-3(2H)-pyridazinone with a dehydrogenating agent, preferably by reaction with bromine in hot acetic acid.

A composition aspect of the invention resides in the cardiotonic composition for increasing cardiac contractility, said composition comprising a pharmaceutically-acceptable inert carrier and, as the active component thereof, an effective amount of a cardiotonic 2-R-6-PY-3(2H)-pyridazinone of (formula I) or pharmaceutically-acceptable acid-addition salt thereof, where R is hydrogen, lower-alkyl or lower-hydroxyalkyl, and PY is defined as in formula I. Preferred embodiments are those where PY is 4-pyridinyl or 3-pyridinyl and R is hydrogen, methyl, ethyl or 2-hydroxyethyl.

In a method aspect, the invention resides in the method for increasing cardiac contractility in a patient requiring such treatment which comprises administering orally or parenterally in a solid or liquid dosage form to such patient an effective amount of a cardiotonic 2-R-6-PY-3(2H)-pyridazinone or pharmaceutically-acceptable acid-addition salt thereof, where R is hydrogen, lower-alkyl or lower-hydroxyalkyl, and PY is defined as in formula I. Preferred embodiments are those where PY is 4-pyridinyl or 3-pyridinyl and R is hydrogen, methyl, ethyl or 2-hydroxyethyl.

The term "lower-alkyl" as used herein, e.g., as one of the meanings for R (formula I) or as a substituent for PY (formula I) means alkyl radicals having from one to six carbon atoms which can be arranged as straight or branched chains, illustrated by methyl, ethyl, n-propyl, isopropyl, n-butyl, 2-butyl, isobutyl.

The symbol PY as used here, e.g., as the 6-substituent in the compounds having formula I, means 4- or 3-pyridinyl or 4- or 3-pyridinyl having one or two "lower-alkyl" substituents, illustrated by 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl", as used herein, e.g., as one of the meanings for R in formula I, means hydroxyalkyl radicals having from two to six carbon atoms and having its hydroxy group and its free valence bond (or connecting linkage) on different carbon atoms which can be arranged as straight or branched chains, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxyamyl, 6-hydroxyhexyl, and the like.

The compounds of the invention having formula I are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base of the cardiotonically-active compounds of the invention are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion-exchange procedures.

The molecular structures of the compounds of the invention were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same, as follows.

The dehydrogenation of 2-R-4,5-dihydro-6-PY-3(2H)-pyridazinone to produce 2-R-6-PY-3(2H)-pyridazinone is preferably carried out by reaction with bromine in hot acetic acid. The reaction is conveniently run at about 80°–120° C., preferably on a steam bath. This dehydrogenation is illustrated hereinbelow in Examples B-1 thru B-15.

The preparation of the intermediate 2-R-4,5-dihydro-6-PY-3(2H)-pyridazinone is carried out by reacting 4-oxo-4-PY-butanenitrile with an N-R-hydrazine salt of a strong inorganic or organic sulfonic acid as illustrated hereinbelow in Examples A-1 thru A-21. The compounds where R is lower-alkyl or lower-hydroxyalkyl and their preparation are disclosed and claimed in copending application Ser. No. 144,564, filed on even date herewith. 4,5-Dihydro-6-(4-pyridinyl)-3-pyridazinol, tautomeric with 4,5-dihydro-6-(4-pyridinyl)-3(2H)-pyridazinone and its preparation are disclosed and claimed in copending Application Ser. No. 71,064, filed Aug. 30, 1979.

The intermediate 4-oxo-4-PY-butanenitriles are generally known compounds, e.g., Stetter et al., Chem. Ber. 107, 210 (1974), and are prepared by generally known methods. Preparation of these compounds is illustrated below in Examples C-1 thru C-6.

The following examples will further illustrate the invention without, however, limiting it thereto.

A. 4,5-Dihydro-2-R-6-PY-3(2H)-pyridazinones [The compounds of Examples A-1 thru A-10 and A-17 thru A-21 and their preparation are disclosed and claimed in copending Application Ser. No. 144,564, filed on Apr. 28, 1980.]

A-1. 4,5-Dihydro-2-methyl-6-(4-pyridinyl)-3(2H)-pyridazinone—To a stirred hot solution containing 25.6 g. of N-methylhydrazine dihydrochloride, 400 ml. of absolute ethanol and 70 ml. of water was added 32 g. of 4-oxo-4-(4-pyridinyl)butanenitrile and the resulting reaction mixture was refluxed overnight (about 15 hours). The solvent was distilled off in vacuo and the resulting solid was recrystallized from ethanol and dried in a vacuum oven at 65° C. overnight to yield 10.5 g. of 4,5-dihydro-2-methyl-6-(4-pyridinyl)-3(2H)pyridazinone as its monohydrochloride, m.p. 219°–225° C. with decomposition.

Acid-addition salts of 4,5-dihydro-2-methyl-6-(4-pyridinyl)-3(2H)-pyridazinone are conveniently prepared by adding to a mixture of 1 g. of 4,5-dihydro-2-methyl-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Also, the lactate or hydrochloride acid-addition salt of 4,5-dihydro-2-methyl-6-(4-pyridinyl)-3(2H)-pyridazinone is conveniently prepared in aqueous solution by adding to water with stirring molar equivalent quantities each of 4,5-dihydro-2-methyl-6-(4-pyridinyl)-(2H)-pyridazinone and lactic acid or hydrochloric acid, respectively.

Following the procedure described in Example A-1 but using in place of N-methylhydrazine dihydrochloride a molar equivalent quantity of the appropriate N-R-hydrazine dihydrochloride or other salt of a strong inorganic acid or organic sulfonic acid, it is comtemplated that there can be obtained the corresponding 4,5-dihydro-2-R-6-(4-pyridinyl)-3(2H)-pyridazinones (or salts thereof) of Examples A-2 thru A-10.

A-2. 2-Ethyl-4,5-dihydro-6-(4-pyridinyl)-3(2H)-pyridazinone.

A-3. 4,5-Dihydro-2-isopropyl-6-(4-pyridinyl)-3(2H)-pyridazinone.

A-4. 4,5-Dihydro-2-n-propyl-6-(4-pyridinyl)-3(2H)-pyridazinone.

A-5. 4,5-Dihydro-2-isobutyl-6-(4-pyridinyl)-3(2H)-pyridazinone.

A-6. 2-n-Hexyl-4,5-dihydro-6-(4-pyridinyl)-3-(2H)-pyridazinone.

A-7. 2-(2-Hydroxyethyl)-4,5-dihydro-6-(4-pyridinyl)-3(2H)-pyridazinone.

A-8. 2-(2-Hydroxypropyl)-4,5-dihydro-6-(4-pyridinyl)-3(2H)-pyridazinone.

A-9. 2-(3-Hydroxypropyl)-4,5-dihydro-6-(4-pyridinyl)-3(2H)-pyridazinone.

A-10. 2-(4-Hydroxybutyl)-4,5-dihydro-6-(4-pyridinyl)-3(2H)-pyridazinone.

A-11. 4,5-Dihydro-6-(4-pyridinyl)-3(2H)-pyridazinone—A mixture containing 2.4 g. of 4-oxo-4-(4-pyridinyl)butanenitrile (same as γ-oxo-γ-(4-pyridinyl)butyronitrile), 1.96 g. of hydrazine sulfate, 100 ml. of absolute ethanol and 100 ml. of water was refluxed with stirring overnight (about 15 hours). The reaction mixture was heated in vacuo to remove the solvent mixture. The remaining residue was taken up in water and filtered. The filtrate was neutralized with 10% aqueous sodium bicarbonate solution and a yellow solid separated. The solid was collected, washed with water, dried in vacuo over P₂O₅ for four hours. Its nuclear magnetic resonance (nmr) and mass spectra were found to be consistent with that of the desired product but showed traces of impurities. The solid was then recrystallized from absolute ethanol, dried in vacuo over P₂O₅ overnight to yield, as golden crystals, 0.9 g. of 4,5-dihydro-6-(4-pyridinyl)-3(2H)-pyridazinone, m.p. 185°–187° C., which is tautomeric with 4,5-dihydro-6-(4-pyridinyl)-3-pyridazinol.

The above reaction also can be run by using a molar equivalent quantity of hydrazine dihydrochloride or hydrazine di(methanesulfonate) in place of hydrazine sulfate.

Acid-addition salts of 4,5-dihydro-6-(4-pyridinyl)-3(2H)-pyridazinone are conveniently prepared by adding to a mixture of 1 g. of 4,5-dihydro-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salts, e.g., hydrochloric, methanesulfonate, sulfate, respectively. Also, the lactate or hydrochloride acid-addition salt is conveniently prepared in aqueous solution by adding to water with stirring molar equivalent quantities each of 4,5-dihydro-6-(4-pyridinyl)-3(2H)-pyridazinone and lactic acid or hydrochloric acid, respectively.

Example A-11 is disclosed as its tautomeric 4,5-dihydro-6-(4-pyridinyl)-3-pyridazinol in Example 1 in copending application Ser. No. 71,064 filed Aug. 30, 1979; and, the tautomer and salts of Example A-11 are claimed in application Ser. No. 71,064.

Following the procedure described in Example A-11 but using in place of 4-oxo-4-(4-pyridinyl)butanenitrile a molar equivalent quantity of the corresponding 4-oxo-4-PY-butanenitrile, it is contemplated that there can be obtained the corresponding 4,5-dihydro-6-PY-3(2H)-pyridazinones of Examples A-12 thru A-16.

A-12. 4,5-Dihydro-6-(3-pyridinyl)-3(2H)-pyridazinone.

A-13. 4,5-Dihydro-6-(2-methyl-3-pyridinyl)-3(2H)-pyridazinone.

A-14. 4,5-Dihydro-6-(5-methyl-3-pyridinyl)-3(2H)-pyridazinone.

A-15. 6-(3-Ethyl-4-pyridinyl)-4,5-dihydro-3(2H)-pyridazinone.

A-16. 4,5-Dihydro-6-(2,6-dimethyl-4-pyridinyl)-3(1H)-pyridazinone.

Following the procedure described in Example A-1 but using in place 4-oxo-4-(4-pyridinyl)butanenitrile a molar equivalent quantity of the appropriate 4-oxo-4-PY-butanenitrile, it is contemplated that the 4,5-dihydro-6-PY-2-methyl-3(2H)-pyridazinones of Examples A-17 through A-21 can be obtained.

A-17. 4,5-Dihydro-2-methyl-6-(3-pyridinyl)-3(2H)-pyridazinone.

A-18. 4,5-Dihydro-2-methyl-6-(2-methyl-3-pyridinyl)-3(2H)-pyridazinone.

A-19. 4,5-Dihydro-2-methyl-6-(5-methyl-3-pyridinyl)-3(2H)-pyridazinone.

A-20. 6-(3-Ethyl-4-pyridinyl)-4,5-dihydro-2-methyl-3(2H)-pyridazinone.

A-21. 4,5-Dihydro-2-methyl-6-(2,6-dimethyl-4-pyridinyl)-3(2H)-pyridazinone.

B. 2-R-6-PY-3(2H)-pyridazinones

B-1. 2-Methyl-6-(4-pyridinyl)-3(2H)-pyridazinone—To a warm solution containing 28 g. of 4,5-dihydro-2-methyl-6-(4-pyridinyl)-3(2H)-pyridazinone monohydrochloride and 140 ml. of acetic acid was added with stirring 100 ml. of bromine, and the resulting reaction mixture was refluxed overnight and then allowed to cool to room temperature. The solid that had separated was collected, stirred with 150 ml. of water and to the aqueous mixture was added sodium bisulfite until bubbling ceased. To the resulting pale yellow solution was added sufficient solid sodium bicarbonate to make it mildly basic to litmus and the resulting mixture was extracted with chloroform. The chloroform extract was heated in vacuo to remove the solvent and the resulting solid was recrystallized from methanol-ether and dried in a vacuum oven at 60° C. overnight to yield 15 g. of 2-methyl-6-(4-pyridinyl)-3(2H)-pyridazinone, m.p. 175°-185° C.

Acid-addition salts of 2-methyl-6-(4-pyridinyl)-3(2H)-pyridazinone are conveniently prepared by adding to a mixture of 1 g. of 2-methyl-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloric, methanesulfonate, sulfate, respectively. Also, the lactate or hydrochloride acid-addition salt of 2-methyl-6-(4-pyridinyl)-3(2H)-pyridazinone is conveniently prepared in aqueous solution by adding to water with stirring molar equivalent quantities each of 2-methyl-6-(4-pyridinyl)-3(2H)-pyridazinone and lactic acid or hydrochloric acid, respectively.

Following the procedure described in Example B-1 but using in place of 4,5-dihydro-2-methyl-6-(4-pyridinyl)pyridazinone or monohydrochloride thereof a corresponding molar equivalent quantity of the appropriate 4,5-dihydro-2-R-6-(4-pyridinyl)pyridazinone or monohydrochloride salt thereof, it is contemplated that the corresponding 2-R-6-(4-pyridinyl)-3(2H)-pyridazinones of Examples B-2 thru B-10 can be obtained.

B-2. 2-Ethyl-6-(4-pyridinyl)-3(2H)-pyridazinone.
B-3. 2-Isopropyl-6-(4-pyridinyl)-3(2H)-pyridazinone.
B-4. 2-n-Propyl-6-(4-pyridinyl)-3-(2H)-pyridazinone.
B-5. 2-Isobutyl-6-(4-pyridinyl)-3(2H)-pyridazinone.
B-6. 2-n-Hexyl-6-(4-pyridinyl)-3(2H)-pyridazinone.
B-7. 2-(2-Hydroxyethyl)-6-(4-pyridinyl)-3(2H)-pyridazinone.
B-8. 2-(2-Hydroxypropyl)-6-(4-pyridinyl)-3(2H)-pyridazinone.
B-9. 2-(3-Hydroxypropyl)-6-(4-pyridinyl)-3(2H)-pyridazinone.
B-10. 2-(4-Hydroxybutyl)-6-(4-pyridinyl)-3(2H)-pyridazinone.

B-11. 6-(4-Pyridinyl)-3(2H)-pyridazinone—A 2 liter 3-necked round bottom flask was equipped with a mechanical stirrer, a reflux condenser and a dropping funnel. Into the flask was placed 750 ml. of acetic acid and 16.3 g. of 4,5-dihydro-6-(4-pyridinyl)-3(2H)-pyridazinone. The mixture was heated on a steam bath for about 20 minutes and then a solution containing 50 ml. of bromine and 150 ml. of acetic acid was initially added dropwise. The first 50 ml. of solution was added over a period of about 20 minutes whereupon solid began precipitating. The rest of the bromine solution was then added all at once followed by the addition of 60 ml. more of bromine. Most of the solid redissolved and the resulting mixture was heated with stirring on a steam bath for 6 hours and then allowed to stand at room temperature over the weekend (about 65 hours). A small amount of crystalline solid was filtered off and the filtrate was heated in vacuo to remove the solvent. The remaining residue was treated with 500 ml. of boiling water whereupon most of the residue dissolved. Sodium bisulfite was added to the hot mixture until bubbling of sulphur dioxide ceased. The mixture was made weakly basic to litmus paper by adding sodium bicarbonate. The solid that separated was collected, recrystallized from isopropyl alcohol and dried in a vacuum oven over $P_2O_5$ at 45° C. for seventeen hours to produce 6.0 g of 6-(4-pyridinyl)-3(2H)-pyridazinone hydrate (6:1), m.p. 222°-224° C.

Acid-addition salts of 6-(4-pyridinyl)-3(2H)-pyridazinone are conveniently prepared by adding to a mixture of 1 g. of 6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Also, the lactate or hydrochloride acid-addition salt of 6-(4-pyridinyl)-3(2H)-pyridazinone is conveniently prepared in aqueous solution by adding to water with stirring molar equivalent quantities each of 6-(4-pyridinyl)-3(2H)-pyridazinone and lactic acid or hydrochloric acid, respectively.

Example B-11 is disclosed as its tautomeric 6-(4-pyridinyl)-3-pyridazinol in Example 2 in copending Application Ser. No. 71,064 filed Aug. 30, 1979; and, the tautomer and salts of Example B-11 are presently claimed in application Ser. No. 71,065.

Following the procedure described in Example B-11 but using in place of 4,5-dihydro-6-(4-pyridinyl)-3(2H)-pyridazinone a molar equivalent quantity of the appropriate 4,5-dihydro-6-PY-pyridazinone, it is contemplated that there can be obtained the corresponding 6-PY-3-(2H)-pyridazinones of Examples B-12 thru B-16.

B-12. 4,5-Dihydro-6-(3-pyridinyl)-3(1H)-pyridazinone.
B-13. 6-(2-Methyl-3-pyridinyl)-3(1H)-pyridazinone.
B-14. 6-(5-Methyl-3-pyridinyl)-3(1H)-pyridazinone.
B-15. 6-(3-Ethyl-4-pyridinyl)-3(1H)-pyridazinone.
B-16. 6-(2,6-Dimethyl-4-pyridinyl)-3(1H)-pyridazinone.

Following the procedure described in Example B-1 but using in place of 4,5-dihydro-2-methyl-6-(4-pyridinyl)-3(2H)-pyridazinone or monohydrochloride thereof a corresponding molar equivalent quantity of the appropriate 2-methyl-6-PY-3(2H)-pyridazinone or monohydrochloride thereof, it is contemplated that the corresponding 2-methyl-6-PY-3(2H)-pyridazinones of Examples B-17 thru B-21 can be obtained.

B-17. 2-Methyl-6-(3-pyridinyl)-3(2H)-pyridazinone.
B-18. 2-Methyl-6-(2-methyl-3-pyridinyl)-3(2H)-pyridazinone.
B-19. 2-Methyl-6-(5-methyl-3-pyridinyl)-3(2H)-pyridazinone.
B-20. 6-(3-Ethyl-4-pyridinyl)-2-methyl-3(2H)-pyridazinone.
B-21. 2-Methyl-6-(2,6-dimethyl-4-pyridinyl)-3(2H)-pyridazinone.

C. 4-Oxo-4-PY-butanenitriles

C-1. 4-Oxo-4-(4-pyridinyl)butanenitrile—To a stirred mixture containing 29.4 g. of sodium cyanide and 500 ml. of acetonitrile, after stirring said mixture for ten minutes, was added dropwise over a period of three hours a solution containing 64.2 g. of 4-pyridinecarboxaldehyde in 500 ml. of acetonitrile and the resulting mixture was stirred at room temperature for one hour. To the stirred mixture was added slowly over a period of one hour a solution of 24.5 g. of acrylonitrile in 200 ml. of acetonitrile and the resulting reaction mixture was stirred overnight at room temperature. The reaction mixture was stripped in vacuo of solvent at a temperature not exceeding 54° C. The semi-solid residue was cooled, mixed well with 400 ml. of chloroform, and the mixture filtered. The chloroform was distilled off in vacuo at a temperature not exceeding 50° C. and the residual oily residue was extracted with three 200 ml. portions of toluene. The toluene solution was filtered through diatomaceous earth and the filtrate was distilled in vacuo below 50° C. to remove the toluene. The residue on chilling crystallized. A tiny sample was saved and the remainder was dissolved in 50 ml. of warm isopropyl alcohol. The solution was cooled and then diluted slowly with 125 ml. of ether, chilled and seeded with a crystal obtained from said tiny sample. The crystalline product that separated was collected, washed with 25 ml. of 1:3 (v:v) mixture of isopropyl alcohol:ether, and air-dried to yield 52.1 g of 4-oxo-4-(4-pyridinyl)butanenitrile, m.p. 53.5°–55° C.

Following the procedure described in Example C-1 but using in place of 4-pyridinecarboxaldehyde a molar equivalent quantity of the appropriate 4- or 3-PY-carboxaldehyde, it is contemplated that there can be obtained the corresponding 4-oxo-4-PY-butanenitriles of Examples C-2 thru C-6, respectively.

C-2. 4-Oxo-4-(3-pyridinyl)butanenitrile.
C-3. 4-(2-Methyl-3-pyridinyl)-4-oxobutanenitrile.
C-4. 4-(5-Methyl-3-pyridinyl)-4-oxobutanenitrile.
C-5. 4-(3-Ethyl-4-pyridinyl)-4-oxobutanenitrile.
C-6. 4-(2,6-Dimethyl-4-pyridinyl)-4-oxobutanenitrile.

The usefulness of the compounds of formula I or salts thereof as cardiotonic agents is demonstrated by their effectiveness in standard pharmacological test procedures, for example, in causing a significant increase in contractile force of the isolated cat atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat atria and papillary muscle procedure, the compounds of formula I or pharmaceutically-acceptable acid-addition salts thereof, e.g., Examples B-1 and B-11, at doses of 30 and/or 100 μg./ml., were found to cause significant increases, that is, greater than 25% in papillary muscle force and significant increases, that is, greater than 25%, in right atrial force, while causing a lower percentage increase in right atrial rate.

When tested by said anesthetized dog procedure, the compounds of formula I or pharmaceutically-acceptable acid-addition salts thereof, e.g., Example B-11, at doses of 0.3, 1.0, 3.0 and/or 10 mg./kg. administered intravenously as a single bolus injection were found to cause significant increases, that is, 25% or greater, in cardiac contractile force or cardiac contractility with lower changes in heart rate and blood pressure.

The present invention includes within its scope a cardiotonic composition for increasing cardiac contractility, said composition comprising a pharmaceutically-acceptable carrier and, as the active component thereof, the cardiotonic compound of formula I or pharmaceutically-acceptable acid-addition salt thereof. The invention also includes within its scope the method for increasing cardiac contractility in a patient requiring such treatment which comprises administering to such patient an effective amount of cardiotonic compound of formula I or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders, and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and perserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 2-R-6-PY-3(2H)-pyridazinone having the formula

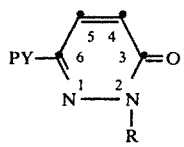

or pharmaceutically-acceptable acid-addition salt thereof, where PY is 4-pyridinyl or 4-pyridinyl having one or two lower-alkyl substituents, and R is hydrogen, lower-alkyl or lower-hydroxyalkyl.

2. A compound according to claim 1 where PY is 4-pyridinyl.

3. A compound according to claim 1 where R is hydrogen.

4. A compound according to claim 1 where R is methyl.

5. A compound according to claim 1 where R is ethyl.

6. A compound according to claim 1 where R is 2-hydroxyethyl.

7. 6-(4-Pyridinyl)-3(2H)-pyridazinone or pharmaceutically-acceptable acid-addition salt thereof.

8. 2-Methyl-6-(4-pyridinyl)-3(2H)-pyridazinone or pharmaceutically-acceptable acid-addition salt thereof.

9. A cardiotonic composition for increasing cardiac contractility, said composition comprising a pharmaceutically-acceptable inert carrier and, as the active component thereof, an effective amount of a cardiotonic 2-R-6-PY-3-(2H)-pyridazinone or pharmaceutically-acceptable acid-addition salt thereof where R is hydrogen, lower-alkyl or lower-hydroxyalkyl, and PY is 4-pyridinyl or 4-pyridinyl having one or two lower-alkyl substituents.

10. The composition according to claim 9 where PY is 4-pyridinyl and R is hydrogen, methyl, ethyl or 2-hydroxyethyl.

11. The composition according to claim 9 where the cardiotonic is 6-(4-pyridinyl)-3(2H)-pyridazinone or pharmaceutically-acceptable acid-addition salt thereof.

12. The composition according to claim 9 wherein the cardiotonic is 2-methyl-6-(4-pyridinyl)-3(2H)-pyridazinone or pharmaceutically-acceptable acid-addition salt thereof.

13. The method for increasing cardiac contractility in a patient requiring such treatment which comprises administering orally or parenterally in a solid or liquid dosage form to such patient an effective amount of a cardiotonic 2-R-6-PY-3(2H)-pyridazinone or pharmaceutically-acceptable acid-addition salt thereof, where R is hydrogen, lower-alkyl or lower-hydroxyalkyl, and PY is 4-pyridinyl or 4-pyridinyl having one or two lower-alkyl substituents.

14. The method according to claim 13 where PY is 4-pyridinyl and R is hydrogen, methyl, ethyl or 2-hydroxyethyl.

15. The method according to claim 13 where the cardiotonic is 6-(4-pyridinyl)-3(2H)pyridazinone or pharmaceutically-acceptable acid-addition salt thereof.

16. The method according to claim 13 where the cardiotonic is 2-methyl-6-(4-pyridinyl)-3(2H)-pyridazinone or pharmaceutically-acceptable acid-addition salt thereof.

* * * * *

UNITED STATES PATENT AND TRADEMARK OFFICE
CERTIFICATE OF CORRECTION

PATENT NO. : 4,304,777

DATED : December 8, 1981

INVENTOR(S) : George Y. Lesher et al.

It is certified that error appears in the above-identified patent and that said Letters Patent are hereby corrected as shown below:

Column 1, line 22, "appliction" should read -- application --.

Column 3, line 10, "are" should read -- for --.

Signed and Sealed this

Ninth Day of November 1982

[SEAL]

Attest:

GERALD J. MOSSINGHOFF

Attesting Officer    Commissioner of Patents and Trademarks